United States Patent
Ramer

(10) Patent No.: US 7,232,461 B2
(45) Date of Patent: Jun. 19, 2007

(54) NECK COVERING DEVICE FOR AN ANEURYSM

(75) Inventor: Marc Ramer, Weston, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 775 days.

(21) Appl. No.: 10/696,691

(22) Filed: Oct. 29, 2003

(65) Prior Publication Data

US 2005/0096728 A1  May 5, 2005

(51) Int. Cl.
  *A61F 2/06* (2006.01)
(52) U.S. Cl. .................... 623/1.28; 623/1.18; 606/200; 606/108
(58) Field of Classification Search ................ 606/200; 623/1.28, 1.18
  See application file for complete search history.

(56) References Cited

U.S. PATENT DOCUMENTS

| 5,830,230 | A | 11/1998 | Berryman et al. |
| 5,925,062 | A | 7/1999 | Purdy |
| 5,951,599 | A | 9/1999 | McCrory |
| 5,980,514 | A | 11/1999 | Kupiecki et al. |
| 6,036,720 | A | 3/2000 | Abrams et al. |
| 6,086,577 | A | 7/2000 | Ken et al. |
| 6,093,199 | A * | 7/2000 | Brown et al. ............... 606/200 |
| 6,183,495 | B1 | 2/2001 | Lenker et al. |
| 6,261,305 | B1 * | 7/2001 | Marotta et al. ............. 606/200 |
| 6,309,367 | B1 | 10/2001 | Boock |
| 6,344,048 | B1 | 2/2002 | Chin et al. |
| 6,613,074 | B1 * | 9/2003 | Mitelberg et al. .......... 623/1.11 |
| 2003/0055451 | A1 * | 3/2003 | Jones et al. ................. 606/200 |
| 2003/0171739 | A1 * | 9/2003 | Murphy et al. ................ 606/1 |
| 2004/0087998 | A1 * | 5/2004 | Lee et al. .................... 606/200 |

FOREIGN PATENT DOCUMENTS

| WO | WO 01/93762 | 12/2001 |
| WO | WO 02/00139 | 1/2002 |

OTHER PUBLICATIONS

U.S. Appl. No. 10/608,659, filed Jun. 2003, Escamilla et al.
Langer R and Lendlein A., "Biodegradable, Elastic Shape-Memory Polymers for Potential Biomedical Applications," Science vol. 296, May 31, 2002, pp. 1673-1676.
European Search Report dated Jun. 15, 2006 for corresponding Appln. No. EP 04 25 6673.

* cited by examiner

*Primary Examiner*—Anhtuan T. Nguyen
*Assistant Examiner*—Elizabeth Houston
(74) *Attorney, Agent, or Firm*—Henry W. Collins

(57) ABSTRACT

An aneurysm neck covering device which is particularly useful for sealing the neck of an aneurysm located in the vicinity of a bifurcated blood vessel. The neck covering device includes a self-expanding stent for supporting and retaining a self-expanding neck cover which seals the neck of the aneurysm.

7 Claims, 6 Drawing Sheets

NECK COVERING DEVICE FOR AN ANEURYSM

BACKGROUND OF INVENTION

1. Field of the Invention

The present invention relates to medical devices used to treat aneurysms within diseased blood vessels, and more particularly, relates to medical devices used to seal the neck of terminal aneurysms which occur in the vicinity of a bifurcated blood vessel.

2. Description of the Prior Art

The use of vascular occlusive medical devices has become a common therapy for the treatment of aneurysms. Aneurysms are often times treated by performing vascular surgery. Vascular surgery allows a physician to access, clip and sometimes remove an aneurysm. This surgical procedure, however, is extremely traumatic and presents a high level of risk, particularly when treating cerebral aneurysms.

To avoid the high risk of vascular surgery, intravascular devices have been used to either cover or fill an aneurysm. For example, grafted stents have been used to cover the neck of an aneurysm and prevent blood flow within the aneurysm. Grafted stents, however, may impede blood flow through blood vessels surrounding the aneurysm. For this reason, grafted stents have limited use in treating aneurysms, particularly terminal aneurysms which occur at or near blood vessel bifurcations.

To fill an aneurysm, various medical devices, such as embolic coils, have been used. Such medical devices are intended to partially fill an aneurysm and promote the formation of thrombus within the aneurysm. The embolic coils and surrounding thrombus prevent further blood flow within the aneurysm and reduce the pressure on the aneurismal wall, thus reducing the risk of rupture. Thrombus within an aneurysm, however, may migrate out of the aneurysm and cause emboli formation downstream, leading to more serious problems, such as ischemic stroke.

An alternative therapy involves placing embolic coils within an aneurysm and supporting the embolic coils within the aneurysm with a stent or other such retaining device. U.S. Pat. No. 6,093,199, entitled "Intra-luminal Device for Treatment of Body Cavities and Lumens and Method of Use," discloses an intraluminal device comprising a flow retainer for maintaining an embolic mass within an aneurysm and an anchoring element for holding the retainer within a blood vessel. U.S. Pat. No. 6,183,495, entitled "Wire Frame Partial Flow Obstruction Device for Aneurysm Treatment," discloses a wire-frame stent for use within the vasculature. The stent includes a flow disrupting region disposed between the ends of the stent for restricting the flow of blood into an aneurysm.

SUMMARY OF THE INVENTION

In accordance with one aspect of the present invention, there is provided a medical device comprised of an expandable stent which takes the form of a skeletal tubular member having a plurality of cells formed by a plurality of interconnected strut members. The medical device further includes a bridge member which takes the form of an elongated sinusoidal element coupled to the distal end of the expandable stent. In addition, the medical device includes an aneurysm cover formed of a shape-memory polymer sheet extending from the distal end of the bridge member so that upon deployment, the aneurysm cover assumes a generally planar configuration. Preferably, the aneurysm cover takes the form of a polymer sheet folded to form a plurality of pleats so that said aneurysm cover may be compressed to facilitate the delivery of the medical device and later expanded upon deployment of the medical device. The aneurysm cover is preferably formed of caprolactone-(poly) lactic acid. Alternatively, the aneurysm cover may be formed of polyurethane. Additionally, the medical device may include an anti-spasmodic or anti-stenosis drug applied as a coating on the aneurysm cover.

In accordance with another aspect of the present invention, there is provided a medical device comprised of an anchor member having a hollow tubular body, a bridge member which takes the form of an elongated wire, and an aneurysm cover which takes the form of an expandable structure. The bridge member is coupled to and extends from the distal end of the anchor member, while the aneurysm cover is coupled to and extends from the distal end of the bridge member. Upon expansion, the aneurysm cover is of a generally planar configuration and is comprised of a shape-memory polymer sheet, such as caprolactone-(poly) lactic acid. The aneurysm cover is similar in construction to a hand held fan.

In accordance with yet another embodiment of the present invention, there is provided a medical device comprised of an anchor member, a bridge member extending from the anchor member, and a blood flow diverter taking the form of a sheet of polymeric material extending from the distal end of the bridge member. The blood flow diverter limits blood flow into an aneurysm when the medical device is deployed adjacent to the aneurysm. The blood flow diverter is preferably comprised of a shape-memory polymer sheet folded to form a plurality of pleats so that the blood flow diverter may be contracted to facilitate in the delivery of the medical device. When the medical device is deployed, the blood flow diverter expands and takes on a generally planar configuration. The blood flow diverter is preferably formed from caprolactone-(poly) lactic acid, and may include a coating of anti-spasmodic or anti-stenosis drugs.

In accordance with still another aspect of the present invention, there is provided a medical device comprised of a tubular anchor portion, a bridge portion which takes the form of a slender rod extending from the anchor portion, and an aneurysm cover portion. The bridge portion is attached to the anchor portion. Additionally, the cover portion is attached to the bridge portion and is comprised of a polymeric sheet folded to form an expandable configuration.

In accordance with another aspect of the present invention, there is provided a medical device comprised of an expandable stent which takes the form of a hollow tubular member. The medical device further includes a first and second bridge member each of which preferably take the form of a sinusoidal shaped element coupled to and extending from the distal portion of the expandable stent in a direction substantially parallel to the longitudinal axis of the expandable stent. A first and a second aneurysm cover are coupled to and extend from the distal end of the first and second bridge member, respectively. The first aneurysm covers are formed of shape-memory polymer sheets folded to form a plurality of pleats. When expanded, the aneurysm covers lie in planes substantially perpendicular to the longitudinal axis of the expandable stent. The first and second aneurysm covers include surfaces which are in planer contact when the medical device is fully deployed within a blood vessel.

DESCRIPTION OF THE PREFERRED EMBODIMENT

Figure 1:
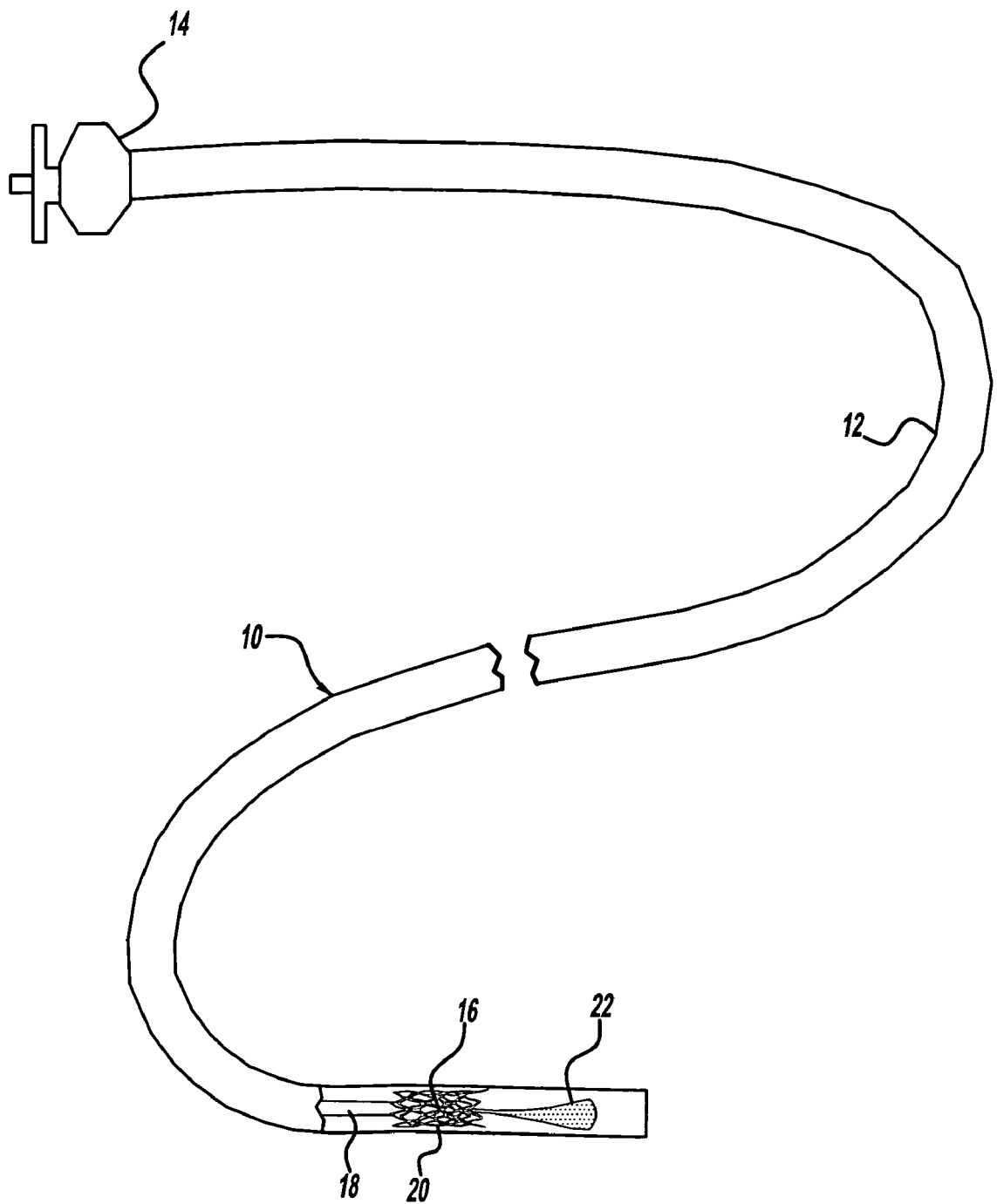
FIG. 1 is a cut-away view which illustrates a medical device for treating an aneurysm in accordance with the present invention positioned within the lumen of a delivery catheter.

FIG. 1 generally illustrates a catheter-based neck covering device 10 for treating an aneurysm, and is particularly suited to treat a terminal aneurysm which occurs at or near a bifurcated blood vessel. More particularly, the catheter-based neck covering device 10 comprises a delivery catheter 12 having a Luer connector 14 which is coupled to the proximal end of the catheter 12. A stent deployed neck covering mechanism 16 is disposed within the lumen of the delivery catheter 12 and is positioned at the proximal end of the catheter 12. An elongated corewire 18 extends from the proximal end of the delivery catheter 12 and is attached to the neck covering mechanism 16 so that once the distal end of the delivery catheter 12 is placed in the desired location within a blood vessel, the elongated corewire 18 may be moved distally in order to launch the neck covering mechanism 16.

As may be noted, the neck covering mechanism 16 includes a self-expanding support stent 20 which supports a self-expanding aneurysm cover member 22 and which, when moved out of the distal end of the delivery catheter 12, expands within a blood vessel to properly position the aneurysm cover member 22 against the neck of an aneurysm.

The self-expanding support stent 20 preferably takes the form of the self-expanding stent disclosed in U.S. patent application Ser. No. 10/608,659, entitled, "Expandable Stent With Radiopaque Markers And Stent Delivery System," filed on Jun. 27, 2003 and assigned to the same assignee as the present patent application. More particularly, the self-expanding stent 20 is held in compression on the elongated corewire 18 until such time as the stent 20 is moved out of the distal end of the delivery catheter 12. When the support stent 20 is moved out of the distal lumen of the delivery catheter 12, the stent expands into contact with the inner wall of a blood vessel. As described in the aforementioned patent application, upon expansion of the stent 20, the interior of the stent moves away from the elongated corewire 18 thereby separating the stent from the guidewire for removal of the corewire 18.

Figure 2:
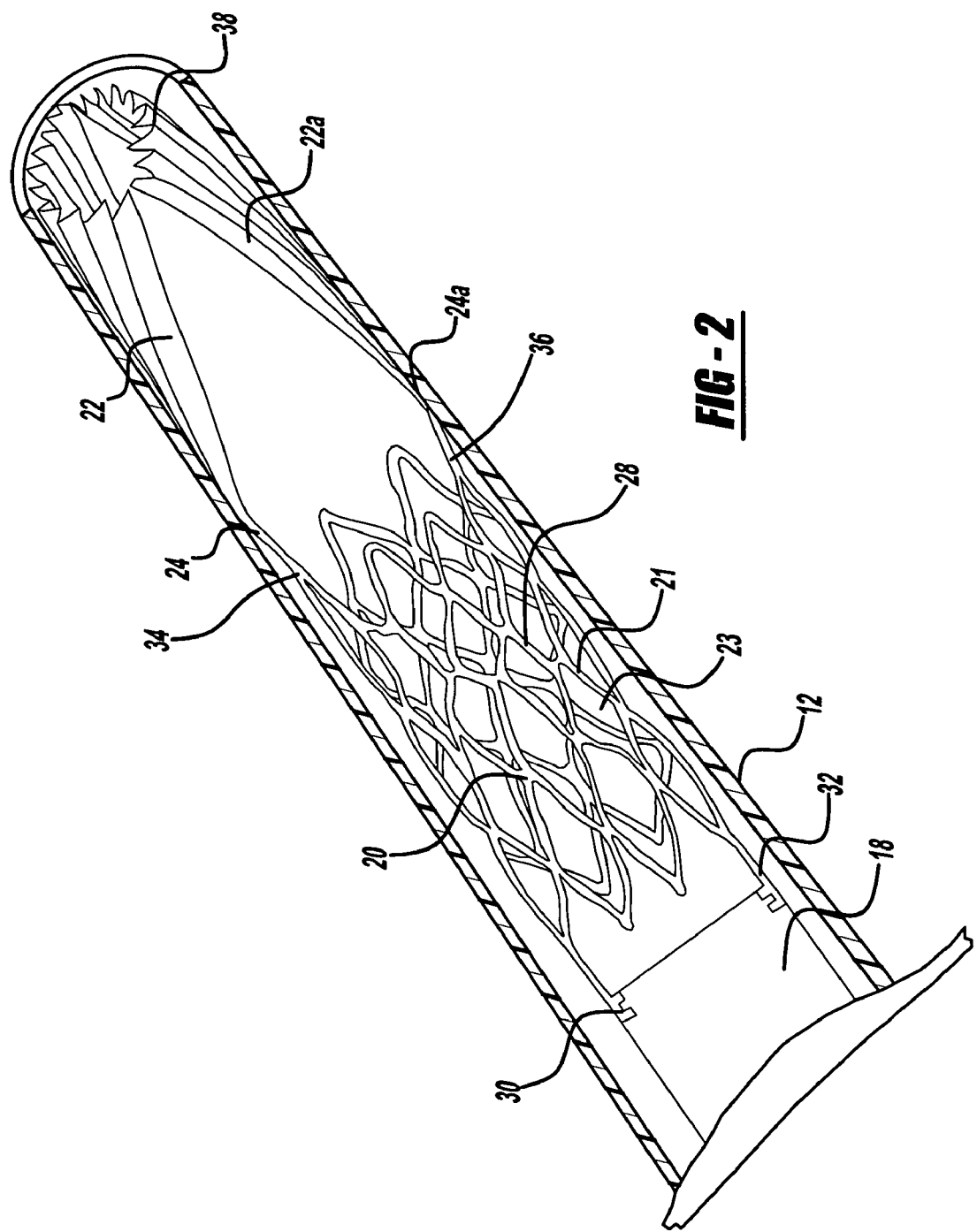
FIG. 2 is a partial sectional view which shows an enlarged view of the medical device shown in FIG. 1 compressed within the lumen of the delivery catheter.

FIG. 2 illustrates in more detail the construction of the self-expanding support stent 20 and the attached self-expanding aneurysm cover members 22, 22a. The aneurysm cover members 22, 22a are coupled to the stent 20 through a pair of sinusoidal-shaped bridge members 24, 24a, respectively.

More particularly, the self-expanding stent 20 is preferably laser cut from a tubular piece of nitinol tubing to form a skeletal tubular member 21. The skeletal tubular member is of a small diameter and has a thin wall comprised of a plurality of cells 23 which are formed by a plurality of interconnected strut members 28. After the nitinol tubular member is cut to form the skeletal member, the material is heated so as to cause the material to exhibit super-elastic properties at body temperature. In addition, the stent 20 includes proximal strut members 30, 32 which serve to engage the elongated corewire 18 prior to the expansion of the stent.

The self-expanding stent 20 also includes two distal strut members 34, 36 which are connected to the bridge members 24, 24a, respectively. The bridge members 24, 24a, are in turn, connected to the self-expanding aneurysm cover members 22, 22a, respectively. The self-expanding stent 20 and the self-expanding aneurysm cover members 22, 22a are held in a compressed state within the inner lumen of the delivery catheter 12 prior to release of the neck covering mechanism 16.

Figure 3:
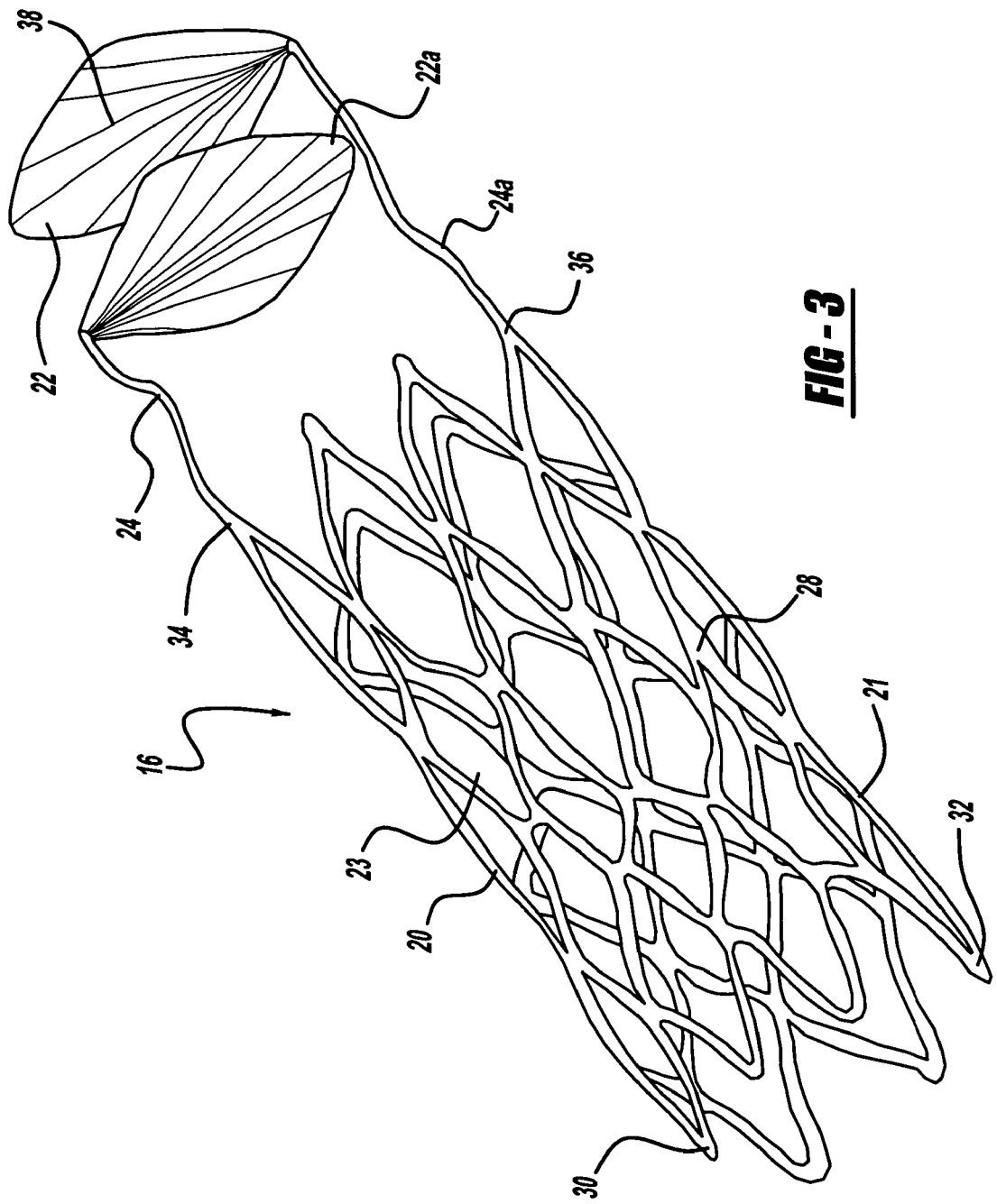
FIG. 3 is an enlarged oblique view of the medical device shown in FIG. 2 in its expanded condition.

FIG. 3 is an oblique view of the neck covering mechanism 16 in its expanded state. More particularly, when the neck covering mechanism 16 is moved out of the distal end of the delivery catheter 12, the self-expanding stent 20 expands to contact the inner walls of a blood vessel to thereby provide support for the aneurysm cover members 22, 22a. Simultaneously, the bridge members 24, 24a bend to thereby cause the aneurysm cover members 22, 22a to move into parallel planes which extend at right angles to the longitudinal axis of the self-expanding stent 20. Also simultaneously, each of the self-expanding aneurysm cover members 22, 22a expand from a folded state into a generally planar configuration in a manner similar to the way a hand-held fan expands from a folded condition to an open condition. In other words, the aneurysm cover members 22, 22a are initially folded in a zigzag fashion along the multiple pleads 38, and upon being released, the cover members 22, 22a open to form generally parallel planar surfaces. The expansion of the support stent 20 and the flexing of the bridge members 24, 24a occur as a result of the nitinol material of which they are fabricated returning to its preprogrammed state. The expansion of the cover members 22, 22a occurs as a result of the shape-memory polymer material of which they are fabricated returning to its preprogrammed state. While shown for illustrative purposes in FIG. 3 as being separated, the aneurysm cover members 22, 22a move into face-to-face contact with each other and provide complimentary planar surfaces for covering a generally circular opening, or neck, of an aneurysm.

As previously indicated, when the self-expanding stent 20 expands, the proximal strut members 30, 32 of the stent move away from the corewire 18 to thereby disengage the corewire so that the corewire may be removed from the stent and from the delivery catheter.

Figure 4:
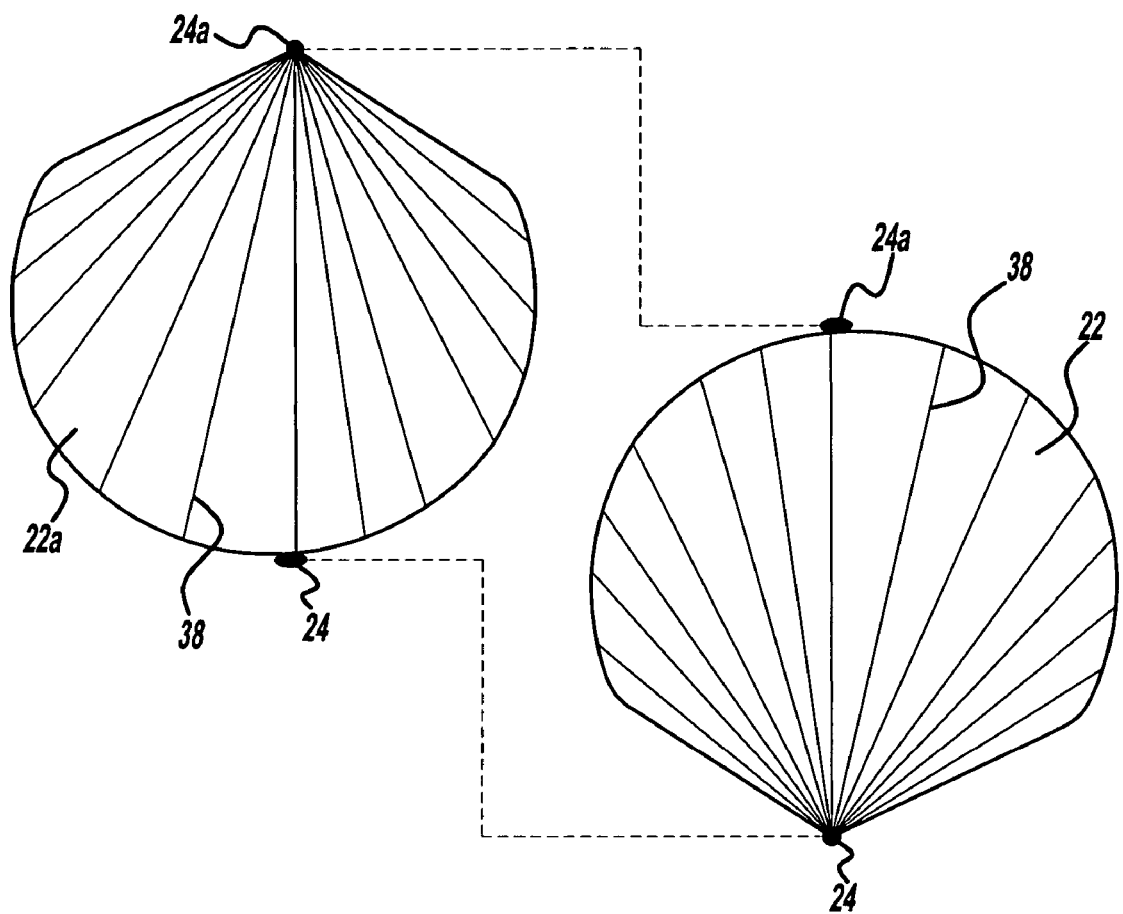
FIG. 4 is an enlarged planar view of the aneurysm covers of the medical device separated for illustrative purposes only.
Figure 5:
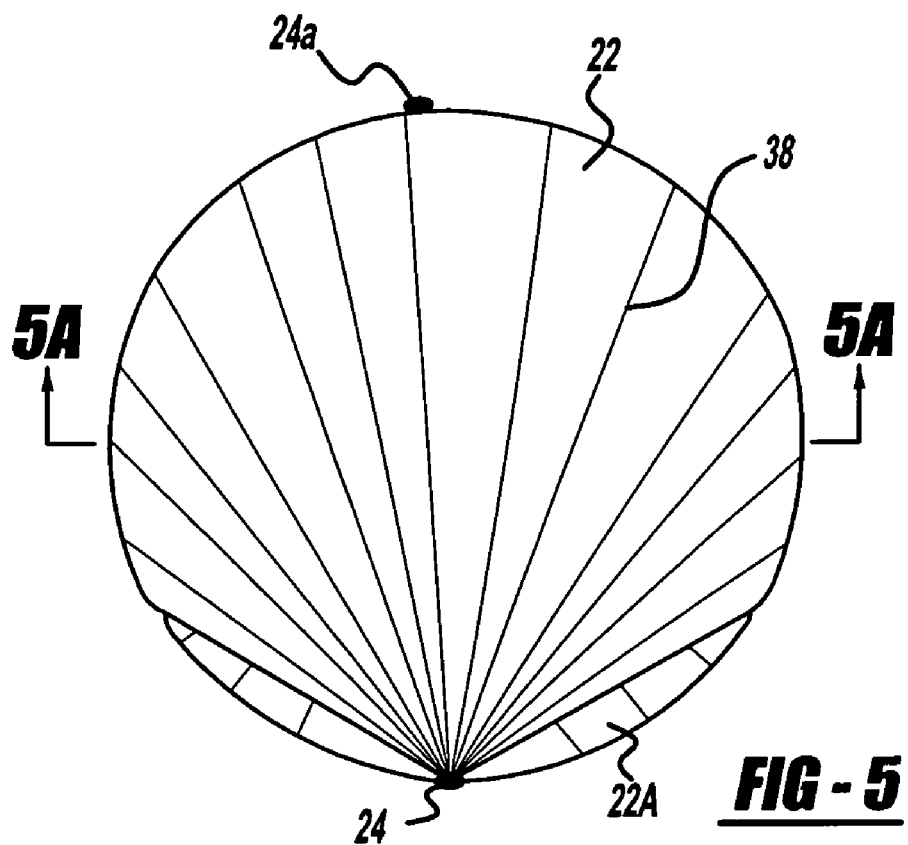
FIG. 5 in an enlarged planar view of the aneurysm covers shown in alignment with each other.
Figure 5A:
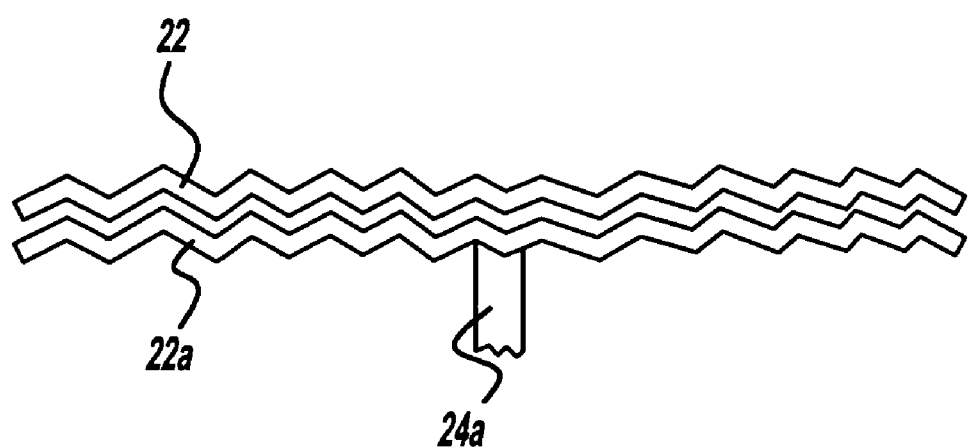
FIG. 5A is a cross-sectional view of the aneurysm covers shown in FIG. 5 taken along the line 5A-5A; and, FIG. 6 is an enlarged view of the medical device shown in FIG. 3 implanted within a bifurcated blood vessel and having the aneurysm covers positioned across the neck of a terminal aneurysm.

FIGS. 4, 5 and 5a illustrate in more detail the construction and orientation of the self-expanding aneurysm cover members 22, 22a. More particularly, and as illustrated in FIG. 4, each of the aneurysm cover members 22, 22a generally take the form of a hand-held fan and, upon expansion, take the form of a generally circular configuration except for two portions extending from the bridge members 24, 24a which are generally straight. In order to create an aneurysm cover which will cover a generally circular neck opening, the aneurysm cover members 22, 22a are oriented, as illustrated in FIGS. 4 and 5, such that when overlapped the covers provide complete coverage for a generally circular opening. If, however, the aneurysm neck opening is somewhat smaller in diameter than the outside diameter of the aneurysm cover members 22, 22a, it is possible that a single aneurysm cover could be used to cover such a neck opening. Accordingly, the neck covering mechanism 16 could include only a single aneurysm cover member 22.

FIG. 5a illustrates in more detail the lateral orientation of the aneurysm cover members 22, 22a, and while shown as being separated from each other for illustrative purposes, the aneurysm cover members 22, 22a would, when expanded, be in face-to-face contact with each other.

Figure 6:
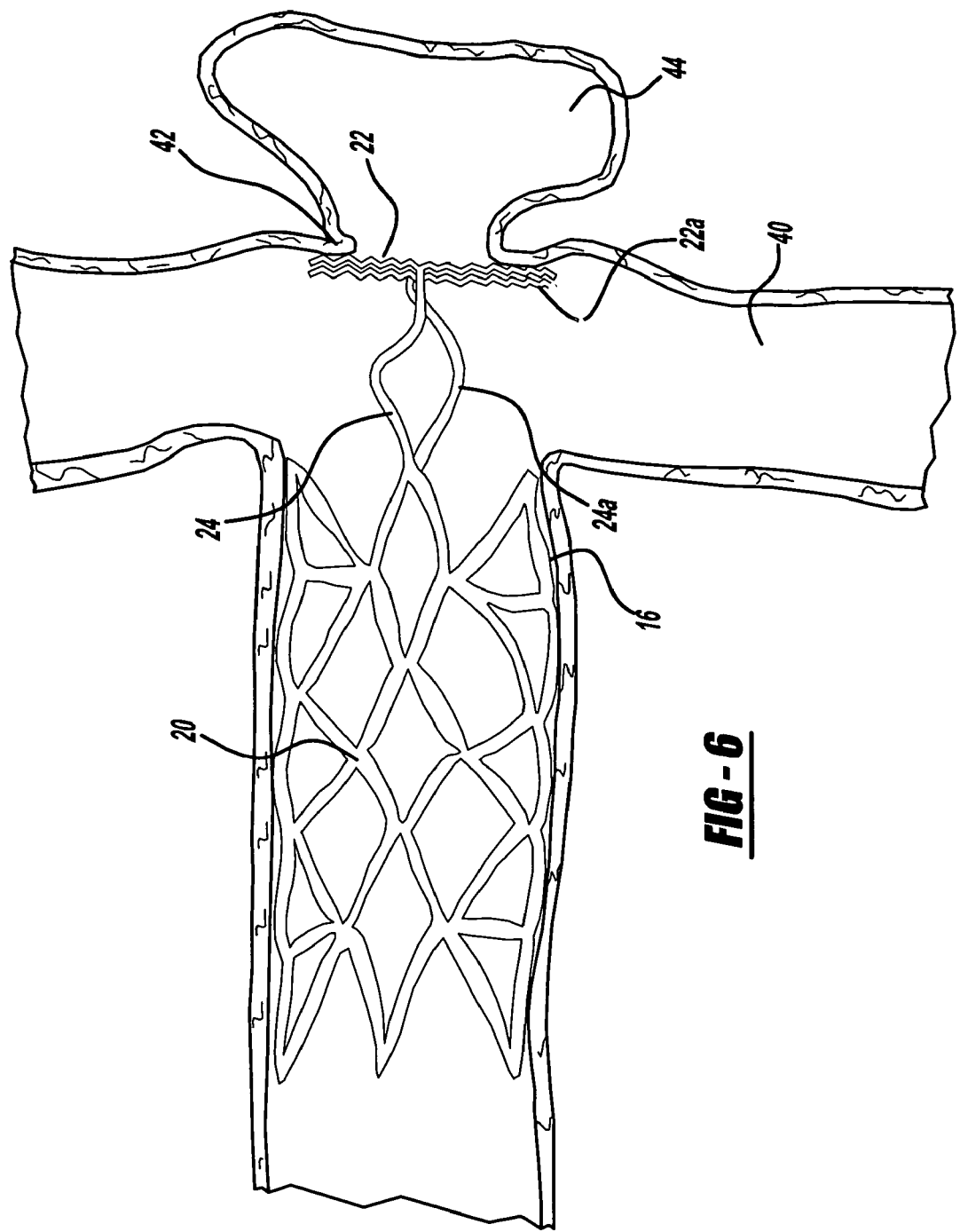

FIG. 6 illustrates the neck covering mechanism 16 positioned within a bifurcated blood vessel 40 with the aneurysm cover members 22, 22a placed across the opening of the neck 42 of an aneurysm 44. More particularly, the self-expanding stent 20 is shown expanded into the inner wall of a blood vessel for providing support for the aneurysm cover members 22, 22a. The bridge members 24, 24a, upon expansion, cause the aneurysm cover members 22, 22a to become oriented such that they lie in planes which extend at right angles to the longitudinal axis of the stent 20. In addition, the aneurysm cover members 22, 22a are shown in expanded configurations so as to provide a continuous covering for a generally circular opening in the neck 42 of the aneurysm 44.

Once the neck to the aneurysm 44 is covered by the aneurysm cover members 22, 22a, blood pressure exerted on the interior of the aneurysm is reduced which will generally cause the aneurysm to cease growing and with the result that there is a significant reduction in risk of rupture of the aneurysm. The aneurysm cover members 22, 22a are preferably coated with an anti-spasmodic material. In addition, it may be desirable to coat the stent 20, or the entire structure of the neck covering mechanism 16 with drugs which prevent stenosis from occurring. It may also be desirable to construct the entire neck covering mechanism 16 out of a material which degrades over a period of time such that the entire structure degrades and dissolves into the blood stream after a period of treatment of the aneurysm.

Although a preferred embodiment of the present invention has been described, it is to be understood that various modifications may be made by those skilled in the art without departing from the scope of the claims which follow. For example, the self-expanding stent 20 and the aneurysm cover member 22, 22a may be fabricated from various biocompatible polymers or metals other than nitinol. These elements may also take the form of various other configurations which, upon being released, expand to provide support and a covering for an aneurysm.

That which is claimed is:

1. A medical device comprised of:
   an expandable stent which takes the form of a hollow tubular member having proximal and distal portions and a longitudinal axis;
   a first bridge member which takes the form of a sinusoidal element having proximal and distal ends, said proximal end of said first bridge member coupled to and extending distally from the distal portion of said expandable stent in a direction substantially parallel to the longitudinal axis of said expandable stent;
   a second bridge member which takes the form of a sinusoidal element having proximal and distal ends, said proximal end of said second bridge member coupled to and extending distally from the distal portion of said expandable stent in a direction substantially parallel to the longitudinal axis of said expandable stent;
   a first self-expanding aneurysm cover formed of a shape-memory sheet initially folded along a plurality of pleats, said first aneurysm cover coupled to and extending from the distal end of said first bridge member and upon expansion becoming planar and lying in a plane substantially perpendicular to the longitudinal axis of said expandable stent; and,
   a second self-expanding aneurysm cover formed of a shape-memory sheet initially folded along a plurality of pleats, said second aneurysm cover coupled to and extending from the distal end of said second bridge member and upon expansion becoming planar and lying in a plane substantially perpendicular to the longitudinal axis of said expandable stent.

2. A medical device as defined in claim 1, wherein said first and second aneurysm covers include first and second planar surfaces, and the first surface of said first aneurysm cover is in planar contact with the second surface of said second aneurysm cover upon expansion of said first and second aneurysm covers.

3. A medical device as defined in claim 2, wherein said aneurysm covers are formed from a polymer.

4. A medical device as defined in claim 3, wherein said aneurysm covers are comprised of caprolactone-(poly) lactic acid.

5. A medical device as defined in claim 3, wherein said aneurysm covers are comprised of polyurethane.

6. A medical device as defined in claim 3, wherein said aneurysm covers are coated with an anti-spasmodic drug.

7. A medical device as defined in claim 3, wherein said aneurysm covers are coated with a drug which inhibits restenosis of a blood vessel.

* * * * *